(12) United States Patent
Orr et al.

(10) Patent No.: US 8,946,433 B2
(45) Date of Patent: Feb. 3, 2015

(54) PROCESS FOR THE PREPARATION OF SUFENTANIL BASE AND RELATED COMPOUNDS

(75) Inventors: Brian Orr, O'Fallon, MO (US); Joseph P. Haar, Jr., Edwardsville, IL (US); George H. Klemm, Webster Groves, MO (US); Keith G. Tomazi, Florissant, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 220 days.

(21) Appl. No.: 13/233,227

(22) Filed: Sep. 15, 2011

(65) Prior Publication Data

US 2012/0071659 A1 Mar. 22, 2012

Related U.S. Application Data

(60) Provisional application No. 61/383,909, filed on Sep. 17, 2010.

(51) Int. Cl.
*C07D 409/06* (2006.01)
*C07D 211/58* (2006.01)

(52) U.S. Cl.
CPC .................................. *C07D 409/06* (2013.01)
USPC .......................................... 546/213; 546/224

(58) Field of Classification Search
CPC .................................................. C07D 409/06
USPC ......................................... 546/223, 213, 244
See application file for complete search history.

(56) References Cited

U.S. PATENT DOCUMENTS

| | | | |
|---|---|---|---|
| 3,998,834 A | 12/1976 | Janssen et al. | |
| 4,179,569 A | 12/1979 | Janssen et al. | |
| 4,584,303 A | 4/1986 | Huang et al. | |
| 5,489,689 A | 2/1996 | Mathew | |
| 7,074,935 B2 * | 7/2006 | Mathew et al. | 546/210 |
| 7,208,604 B2 | 4/2007 | Mathew et al. | |
| 2006/0149071 A1 | 7/2006 | Mathew et al. | |
| 2010/0016365 A1 | 1/2010 | Gant et al. | |

FOREIGN PATENT DOCUMENTS

| | | |
|---|---|---|
| EP | 0677522 | 10/1995 |
| WO | 0140184 | 6/2001 |
| WO | 20060046024 | 5/2006 |

OTHER PUBLICATIONS

Clariant "Your accelerator" p. 1-24 (1998).*
"Crown ether" Wikipedia (2013).*
"Dispersion" Wikipedia (2013).*
"Green Chemistry" Fisher Sci. Ed. p. 1-121 (2013).*
Pfizer "solvent guide" p. 1 (2013).*
"Solvent" Wikipedia p. 1-8 (2013).*
Niemegeers et al., "Sufentanil, a very potent and extremely safe intravenous morphine-like compound in mice, rats and dogs", Arzneimittel-Forschung, 1976, pp. 1551-1556, vol. 26, No. 8.

* cited by examiner

*Primary Examiner* — Celia Chang

(57) ABSTRACT

The present disclosure generally related to an improved process for the preparation of various piperidine derivatives. More particularly, the present disclosure related to an improved process for preparing sufentanil base (1) and related compounds, which advantageously utilizes more cost effective and/or less hazardous reagents, including a dispersion comprising between about 50% and about 70% by weight (based on the total weight of the dispersion) of an alkali metal hydride, such as sodium hydride, as well as eliminates the need for expensive and/or time consuming purification techniques.

(1)

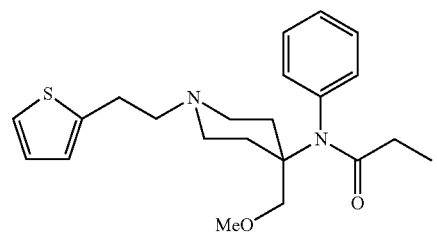

14 Claims, No Drawings

PROCESS FOR THE PREPARATION OF SUFENTANIL BASE AND RELATED COMPOUNDS

CROSS REFERENCE TO RELATED APPLICATIONS

This application claims the benefit of U.S. Provisional Application No. 61/383,909 filed Sep. 17, 2010, which is incorporated herein in its entirety.

BACKGROUND OF THE DISCLOSURE

The present disclosure generally related to an improved process for the preparation of various piperidine derivatives. More particularly, the present disclosure related to an improved process for preparing sufentanil base (1) and related compounds, which advantageously utilizes more cost effective and/or less hazardous reagents, as well as eliminates the need for expensive and/or time consuming purification techniques.

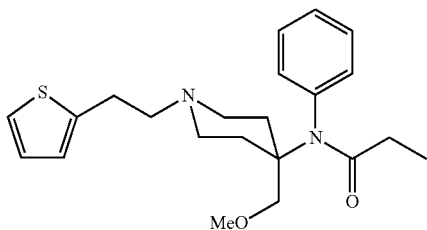

(1)

Sufentanil citrate, the citrate salt of Sufentanil (1), was first reported by Niemegeers et al (Arzneim. Forsch. 26:1551-1556, 1976). It is a piperidine derivative and a member of a series of potent fentanyl analogues. It is a powerful analgesic with an excellent safety margin as compared to other narcotic agents. It is furthermore characterized by a high selectivity and affinity (approximately 10 times greater than fentanyl) for "mu" opiate receptors. Sufentanil citrate produces, unlike fentanyl or morphine, complete anesthesia with minimal side-effects. When compared with fentanyl, its pharmacokinetic profile in humans shows a smaller volume of distribution, resulting in a terminal half-life intermediate between alfentanil and fentanyl. Sufentanil citrate, in high doses with 100% oxygen in patients undergoing major surgical procedures, produces excellent cardiovascular stability and preserves cardiac output and myocardial oxygen balance with minimal changes in heart rate. Sufentanil citrate suppresses most hormonal responses to surgical stimulation, without producing significant cardiovascular depression. Additionally, sufentanil citrate, like fentanyl, does not cause histamine release.

In low to moderate doses, sufentanil citrate may have further advantages over other narcotic agents. For example, when compared with meperidine, morphine and fentanyl in patients undergoing general surgery under balanced anesthesia, sufentanil citrate provides stable cardiovascular parameters, low preoperative catecholamine plasma levels, very little need for additional inhalation supplementation, and a low incidence of postoperative respiratory depression. Because of its remarkably low cardiovascular toxicity, sufentanil citrate has been evaluated as a total intravenous anesthetic for major surgical procedures. It is primarily used for open heart surgery and major operations in patients with severe cardiovascular compromise.

The chemical name for sufentanil citrate is N[4-(methoxymethyl)-1[2-(2-thienyl)ethyl]-4-piperidinyl]-N-phenyl-propanamide 2-hydroxy-1,2,3-propanetricarboxylate, and it has an empirical formula of $C_{28}H_{38}N2O_9S$. Sufentanil citrate is a white crystalline powder (molecular weight approximately 578.7 g) with a reported melting point of approximately 136.3° C. Additionally, it is soluble in most alcohols.

Synthesis of sufentanil base (1) is disclosed, for example, in U.S. Pat. No. 3,998,834 (to Janssen). The process described therein, however, is somewhat lengthy and complicated. Improved procedures were published in U.S. Pat. Nos. 5,489,689 (to Mathew) and 7,208,604 (to Mathew et al.); however, these procedures contain steps that are problematic to scale-up, such as chromatography with diethyl ether, the use of flammable reagents (e.g., 95 wt % sodium hydride dispersion), and/or the use of reagents that are the expensive and difficult to acquire in large quantities (e.g., 15-crown-5 ether as a reaction co-solvent). Accordingly, there continues to be a need for an improved procedure for the preparation of the synthetic opioid, sufentanil, as well as other related compounds. Preferably, such an improved process would be more cost effective, and/or safer to perform, particularly on a production scale, than currently used processes.

BRIEF DESCRIPTION OF THE DISCLOSURE

Briefly, therefore, the present disclosure is directed to an improved process for the preparation of piperidine derivative, and in particular sufentanil or a compound structurally similar or related thereto. The process comprises: (i) contacting a substituted 4-hydroxymethyl-4-aminopiperidine with a dispersion comprising between about 50% and about 70% by weight (based on the total weight of the dispersion) sodium hydride, optionally in the presence of an alcohol catalyst, to deprotonate the hydroxyl group of the substituted 4-hydroxymethyl-4-aminopiperidine; and, (ii) reacting an alkylating agent with the deprotonated, substituted 4-hydroxymethyl-4-aminopiperidine to form an ether derivative thereof. In one particular embodiment of the process, the alkylating agent is a methylating agent and/or the alcohol catalyst is an alkyl alcohol. In a more particular embodiment, the substituted 4-hydroxymethyl-4-aminopiperidine is (4-phenylamino)-1-(2-(thiophen-2-yl)-ethyl-piperidin-4-yl)methanol, the alkylating agent is a methyl iodide, and/or the alcohol catalyst is t-butanol, the resulting piperidine derivative being (4-methoxymethyl)-N-phenyl-1-(2-(thiophen-2-yl)-ethyl-piperidin-4-amine.

The present disclosure is further directed to one or more of the above-described processes, which additionally comprises: (iii) contacting the ether derivative of the substituted 4-hydroxymethyl-4-aminopiperidine with an alkyl acid halide in an organic solvent to form an amide derivative thereof; (iv) removing a portion of the organic solvent from the amide derivative; and, (v) collecting the amide derivative. In one particular embodiment of the process, the alkyl acid halide is an alkyl acid chloride, and more particularly is propionyl chloride. In this or another alternative embodiment, between about 70% and about 80% (by volume) of the organic solvent is removed from the amide derivative. In one of the preceding embodiments, or an alternative embodiment, the ether derivative contacted by the alkyl acid halide is (4-methoxymethyl)-N-phenyl-1-(2-(thiophen-2-yl)-ethyl-piperidin-4-amine, and the resulting amide derivative is sufentanil, either in an acid salt form (e.g., a hydrochloride salt) or the base form (upon optional neutralization of the acid salt form). In one of the preceding embodiments, or an alternative embodiment, collection of the amide comprises in situ recrystallization of the acid salt, followed by conversion to the base form.

The present disclosure is still further directed, in one preferred embodiment, to a process for preparing sufentanil base. The process comprises: (i) preparing a purified 4-(methoxymethyl)-N-phenyl-1-(2-(thiophen-2-yl)ethyl)piperidin-4-amine, the process comprising: (a) combining (4-phenylamino)-1-(2-(thiophen-2-yl)ethyl-piperidin-4-yl)methanol with a dispersion comprising about 60% by weight sodium hydride in the presence of an alcohol catalyst to form a first reaction mixture; (b) heating the first reaction mixture to a temperature between about 65° C. and about 70° C. for about 2 hours to deprotonate the (4-phenylamino)-1-(2-(thiophen-2-yl)ethyl-piperidin-4-yl)methanol; (c) adjusting the temperature of the resulting mixture containing the deprotonated (4-phenylamino)-1-(2-(thiophen-2-yl)ethyl-piperidin-4-yl)methanol to between about 5° C. and about 10° C.; (d) adding an alkylating agent to the temperature adjusted solution, while maintaining the temperature thereof to between about 5° C. and about 10° C., to form a crude 4-(methoxymethyl)-N-phenyl-1-(2-(thiophen-2-yl)ethyl)piperidin-4-amine; (e) isolating the crude 4-(methoxymethyl)-N-phenyl-1-(2-(thiophen-2-yl)ethyl)piperidin-4-amine by adding water thereto and then filtering; (f) purifying the isolated crude 4-(methoxymethyl)-N-phenyl-1-(2-(thiophen-2-yl)ethyl)piperidin-4-amine by liquid-liquid extraction in a solvent system comprising an organic phase and an aqueous phase at a pH between about 5.0 and about 5.2, the organic phase soluble 4-(methoxymethyl)-N-phenyl-1-(2-(thiophen-2-yl)ethyl)piperidin-4-amine being partitioned into the aqueous phase by adjusting the pH thereof to between about 2.0 and about 2.7; and, (g) isolating the 4-methoxymethyl)-N-phenyl-1-(2-(thiophen-2-yl)piperidin-4-amine by adjusting the pH of the partitioned aqueous phase to a pH of greater than about 12 by the addition of a base thereto; and, (ii) converting the purified 4-(methoxymethyl)-N-phenyl-1-(2-(thiophen-2-yl)ethyl)piperidin-4-amine to sufentanil base, the process comprising: (a) reacting the purified 4-(methoxymethyl)-N-phenyl-1-(2-(thiophen-2-yl)ethyl)piperidin-4-amine in a reaction mixture comprising propionyl chloride and an organic solvent, to form an amide derivative thereof; (b) subjecting the resulting reaction mixture to distillation to remove between about 70% and about 80% (by volume) of the organic solvent therefrom; (c) adding HCl to the reaction mixture to form sufentanil HCl; (d) subjecting the resulting sufentanil HCl mixture to further distillation to remove remaining organic solvent; and, (e) adding base to the distilled sufentanil HCl mixture to form sufentanil base. Optionally, prior to base addition, the sufentanil HCl in the distilled mixture may be recrystallized in situ by dissolution in an aqueous alcohol solution, followed by the optional treatment with charcoal and filtration to isolate and/or collect the recrystallized sufentanil HCl.

The present disclosure is still further directed to one or more of the preceding processes, wherein the process consists of, or alternatively consists essentially of, the recited steps.

DETAILED DESCRIPTION OF THE DISCLOSURE

In accordance with the present disclosure, an improved process for the preparation of various piperidine derivatives in general, and in particular a sufentanil base (1) or compounds structurally similar or related thereto, has been discovered. More specifically, an improved process has been discovered that enables the preparation of such compounds on a production scale using more cost effective and/or less hazardous reagents, as well as reducing or eliminating the need for expensive and/or time consuming purification techniques.

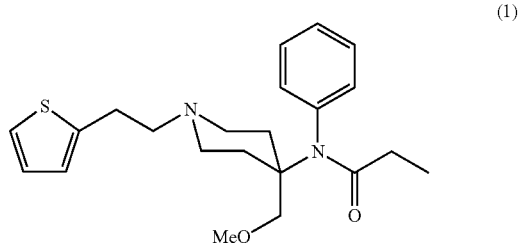 [SMILES: CCC(=O)N(c1ccccc1)C1(COC)CCN(CCc2cccs2)CC1]

(1)

As further detailed herein below, it has been discovered that such compounds may be prepared by a process in which a select substituted 4-hydroxymethyl-4-aminopiperidine is initially converted to a desired ether intermediate in a reaction that utilizes a dispersion of an alkali metal halide, and more specifically sodium hydride, as a reagent in a less concentrated form (as compared, for example, to conventional processes that utilize 95% sodium hydride, which is more flammable), and/or using solvents that are less expensive and/or more commercially available (as compared, for example, to crown ether solvents, such as 15-crown-5 ether). Additionally, it has been discovered that the ether intermediate may be further converted to the desired end product or compound (either in acid salt or base form), by means of reaction with a desired alkyl acid halide, followed by an initially more cost-effective, and/or less aggressive or complete, distillation step, as well as the use of in situ recrystallization of the acid salt, followed by optional basification (to obtain the final base form of the compound).

In this regard it is to be noted that, as used herein, "piperidine derivative" generally refers to a compound having a substituted piperidine core structure, and more specifically refers to a compound having a substituted 4-alkoxyalkyl-4-aminopiperidine (e.g., a 4-methoxymethyl-4-aminopiperidine) core structure. In this regard it is to be further noted that "substituted" typically refers to the presence of a substituent on the nitrogen atom of the piperidine ring (the nitrogen atom thus being at least a tertiary amine). It is to be still further noted that, as used herein, a "less concentrated" alkali metal halide dispersion, such as a dispersion comprising sodium hydride etc., generally refers to a dispersion comprising an alkali metal halide in an appropriate medium or solvent (e.g., mineral oil), the alkali metal halide concentration therein being less than about 70%, 65%, or even 60%, the concentration for example ranging from about 50% to about 70%, or from about 55% to about 65%, and preferably being about 60% (by weight of the overall dispersion). It is to be still further noted that, as used herein, a "less aggressive" or "less complete" distillation generally refers to a distillation in which only a portion of the solvent is removed; that is, the reaction product mixture (which contains the desired end product of compound) is not distilled to dryness. Rather, distillation is typically carried out until about 50% to less than 100% (by volume of the reaction solvent), or between about 60% and about 90%, or between about 70% and about 80%, of the solvent is removed. It is to be still further noted that, as used herein, an "in situ" recrystallization typically refers generally to a recrystallization that occurs within the same reaction vessel (or pot) used in the distillation step, and/or recrystallization from the remains of the reaction mixture itself, thus eliminating additional handling or processing steps (e.g., separation or purification steps), the recrystallization being carried out by means of appropriate solvent addition (as further detailed elsewhere herein below). Finally, it is to be still further noted that, as used herein, "production scale" (or alternatively "commercial scale") generally refers to a scale of hundreds of grams, up to several kilograms, or more (e.g., 100 g, 500 g, 1000 g, 2000 g, 3000 g, or more).

1. Preparation of 4-Hydroxymethyl-4-Aminopiperidine Ether Intermediate

In accordance with the process of the present disclosure, a starting piperidine compound having the general structure of formula (A), below, may be prepared using means generally known in the art (see, e.g., U.S. Pat. Nos. 5,489,689 and 7,208,604, the entire contents of which are incorporated herein by reference for all relevant and consistent purposes):

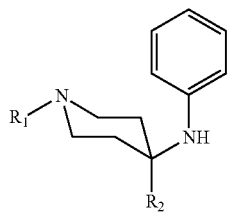

(A)

wherein: $R_1$ is typically substituted alkyl, and more specifically is heterocycloalkyl (e.g., $C_1$-$C_5$ heterocycloalkyl, and in particular is thiophenylethyl, and even more particularly is 2-thiophen-2-ylethyl), and $R_2$ is typically hydroxyalkyl (e.g., $C_1$-$C_5$ hydroxyalkyl), and more specifically is hydroxymethyl. In one or more particular embodiments, the starting compound of the present disclosure is a substituted 4-hydroxymethyl-4-aminopiperidine, and more particularly is a compound having structure (B), below:

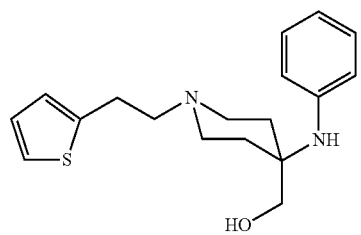

(B)

wherein the compound may be prepared by means generally known in the art (see, e.g., U.S. Pat. No. 7,208,604, Example 9 and Scheme IV, compound 5, the entire contents of which are incorporated herein by reference for all relevant and consistent purposes), and/or as further detailed herein below.

A. Preparation of Exemplary Starting Piperidine Compound

As noted above, the starting piperidine compound of the present disclosure may be prepared by means generally known in the art. In accordance with one exemplary embodiment, and as further illustrated below, a suitable starting piperidine compound may be prepared by condensing a piperidone with a primary amine, such as aniline, so as to form a 4-amino-4-carboxyamino-piperidine. In some exemplary embodiments, the ring nitrogen (N) of one or both the piperidone and the 4-amino-4-carboxyamino-piperidine includes a —COO—$(CH_2)_n$—$CH_3$ substituent, wherein n is an integer of from 0 to about 10. In a more specific embodiment, the piperidone is 1-carbethoxy-4-piperidone, and the 4-amino-4-carboxyamino-piperidine is 1-(carbethoxy)-4-(phenylamino)-4-piperidine carboxanilide, the structure of which is illustrated below.

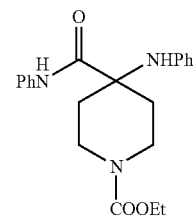

In some embodiments, the primary amine with which the piperidone is condensed is aniline. In one particular exemplary embodiment, the piperidone is reacted with chloroform to form an intermediate epoxide, and then the epoxide is reacted with the primary amine so as to form the 4-amino-4-carboxyamino-piperidine, in accordance with the following Exemplary Scheme.

Exemplary Scheme

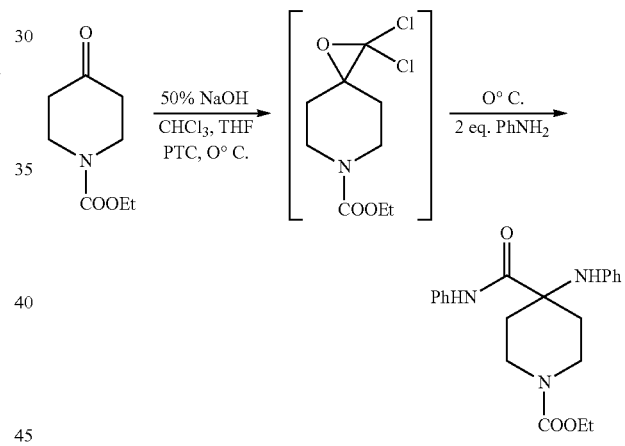

As can be seen in the Exemplary Scheme, the epoxide formed therein is a dichloroepoxide. In accordance with this embodiment, the epoxide is reacted with the aniline so as to form the compound shown above.

In accordance with one aspect of processes described herein, a 4-amino-4-carboxyamino-piperidine, in which the piperidine ring N includes a —COO—$(CH_2)_n$—$CH_3$ substituent, is hydrolyzed so as to remove the substituent attached to the ring N, and form a piperidine hydrolysis product. This ring N substituent can be hydrolyzed with an excess of alkali base, such as KOH, in an organic solvent such as isopropyl alcohol. In some exemplary embodiments, the piperidine hydrolysis product thus formed is a 4-(phenylamino)-4-piperidinecarboxanilide. This piperidine hydrolysis product may then be condensed with a mesylate (methanesulfonyl) of the formula R—$(CH_2)_m$-O-Ms (wherein R is, for example, a heterocyclic moiety, such as thienyl, m is an integer of from about 1 to about 10, or about 1 to about 5, and in particular is 2, and Ms is methanesulfonyl). The resulting product is an N-substituted R—$(CH_2)_m$-piperidine product is shown below (wherein m is 2 and R is thienyl).

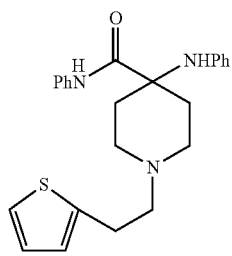

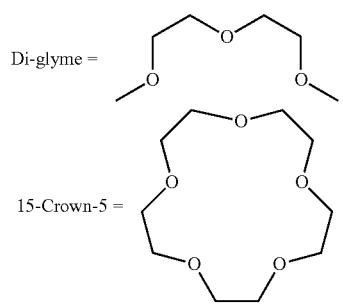

A tertiary amide can also be produced by alkylating the 4-amino-4-carboxyamino-piperidine described above. In certain exemplary embodiments, the tertiary amide is an anilide, as shown below.

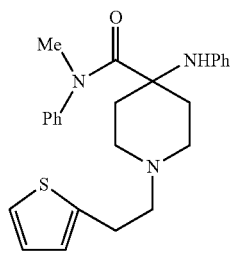

The tertiary amide produced may then be reduced, so as to form an alcohol. In certain exemplary embodiments, the tertiary amide is reduced to the alcohol with a super hydride, such as lithium triethylborohydride, in the presence of an inert organic solvent such as tetrahydrofuran (THF). The alcohol produced according to the general scheme above is N-(2-thien-2-ylethyl)-4-(phenylamino)-4-(hydroxymethyl) piperidine (i.e., compound (2) in Scheme 1, below). In this regard it is to be noted that a similar approach may be taken to prepare other substituted, 4-hydroxymethyl-4-aminopiperidine compounds (as further detailed elsewhere herein below).

B. Preparation of Piperidine Ether Intermediate

As previously noted, the process of the present disclosure comprises first contacting, for example, the substituted 4-hydroxymethyl-4-aminopiperidine, with a dilute dispersion comprising an alkali metal hydride in an appropriate solvent or medium (e.g., one that enables the alkali metal hydride to be safely handled, such as mineral oil), optionally in the presence of a catalyst, in order to deprotonate the hydroxyl group of the noted piperidine derivative. In one particular embodiment, the dispersion comprises between about 50% and about 70%, or from about 55% to about 65%, and preferably about 60%, by weight (based on the total weight of the dispersion) of an alkali metal hydride in, for example, mineral oil. Additionally, the reaction mixture that is formed from these components (i.e., the piperidine compound, the alkali metal dispersion and the catalyst) comprises an appropriate organic solvent, which may be selected for example from the group consisting of diglyme (i.e., diethylene glycol dimethyl ether, as illustrated below), N,N-dimethyl formamide (DMF), 1-methyl-2-pyrrolidinone (NMP), dimethoxy ethane (glyme), diethylene glycol diethyl ether, dimethyl sulfoxide (DMSO), or some combination thereof. In one particular embodiment, diglyme is the preferred solvent, in particular because it is readily available and/or relatively inexpensive (as compared, for example, to the 15-crown-5 ether illustrated below, that is used in other known processes).

In various embodiments, the alkali metal hydride is sodium hydride, while the catalyst is a lower alkyl alcohol (i.e., $C_1$-$C_5$ alcohol), such as t-butanol, isopropanol, ethanol or methanol (or a combination or mixture thereof). The concentration of the various components in the reaction mixture can, in general, be optimized in order to achieve a desired balance of, for example, yield and purity of the end product. Typically, however, the molar ratio of the alkali metal hydride to the piperidine derivative in the reaction mixture will be at least about 1:1, and preferably will be such that a molar excess of the alkali metal hydride is present (the ratio being, for example, between about 1.1:1 and about 1.8:1, or about 1.2:1 and about 1.6:1, with a ratio of about 1.4:1 being preferred in various embodiments). Similarly, when present, the concentration of the alcohol catalyst, and more specifically the alkyl alcohol catalyst, may be optimized, as well. Typically, however, a small, catalytic amount of the alkyl alcohol will be used, such as for example about 0.1, about 0.12, about 0.14, about 0.16, about 0.18, or even about 0.2 equivalents of the alcohol per equivalent of the piperidine derivative.

Like the selection of components, and/or the concentration (or ratio) of the components, used in accordance with the present disclosure, the time and temperature of the reaction may also be optimized in order to achieve a desired balance of, for example, yield and purity of the desired end product. Typically, however, the deprotonation reaction will be carried out at a temperature of between about 50° C. and about 80° C., or between about 60° C. and about 75° C., with a temperature of between about 65° C. and about 70° C. being preferred in various embodiments. The reaction may be allowed to continue at this temperature for a duration of, for example, about 1 hour to about 3 hours, or about 1.5 hours to about 2.5 hours, with a duration of about 2 hours being preferred in various embodiments.

After the deprotonation reaction has reached a desired point of completion (which may be determined by means generally known in the art), the intermediate, deprotonated compound or salt (e.g., a sodium or potassium salt) that is formed may be further reacted (with or without first being isolated) with an alkylating agent to form an ether derivative thereof. Selection of the alkylating agent, as well as the amount used thereof, may be done by means generally known in the art, in order to achieve the desired product. In one particular embodiment, however, the alkylating agent is an alkyl halide, sulfate, tosylate, mesylate, triflate, or another labile leaving group generally known in the art (i.e., $C_1$-$C_5$—X, where the leaving group X is for example: iodide, bromide, sulfate, tosylate, mesylate or triflate, etc.), and more particularly is a methyl halide, such as methyl iodide. The molar ratio of the alkylating agent to the deprotonated intermediate compound (e.g., the sodium or potassium salt of the piperidine derivative) may vary, but typically it will be present in a slight excess (the ratio being, for example, within the range of about 1.05:1 to about 1.15:1, with a ratio of about 1.1:1 being preferred in various embodiments).

The alkylation reaction is typically carried out at a relatively low temperature, and therefore the reaction mixture temperature may need to be adjusted (e.g., cooled). Typically, the reaction mixture temperature is adjusted as needed such that the reaction is carried out at a temperature between for example about 2° C. and about 20° C., or about 4° C. and about 15° C., with a range of between about 5° C. and about 10° C. being preferred. Without being held to any particular theory, it is generally believed that carrying out the reaction at a relatively low temperature helps to minimize the formation of a quaternary salt at a nitrogen atom present in the piperidine derivative, and/or N-alkylation at a benzylic nitrogen atom present therein. The alkylation reaction may be carried out until the desired yield and/or purity of the resulting alkylated reaction product is achieved. Typically, however, the duration of the reaction will be, for example, between about 12 hours and about 18 hours, or about 14 hours and about 16 hours, with about 16 hours being preferred in various embodiments.

After the reaction has been completed, the desired reaction product (i.e., the crude ether) may be isolated from the reaction mixture by means generally known in the art, but more particularly may be isolated by the addition of water thereto and then filtering the resulting mixture. Once isolated, the crude ether may be further purified by a liquid-liquid extraction (as further detailed herein below), followed by partitioning into the aqueous phase thereof. Without being held to any particular theory, it is generally believed that solvent partitioning performs a number of functions, and/or provides a number of benefits over existing methods for preparing such compounds, particularly those used for production-scale processes (e.g., normal phase silica gel chromatography with diethyl ether).

In this regard it is to be noted that, for those embodiments wherein the reaction is carried out in the absence of a catalyst (e.g., an alcohol catalyst), the resulting reaction product mixture may contain higher levels of the starting compound (e.g., the piperidine derivative). In such embodiments, additional purification steps may be needed, and/or may need to be repeated (e.g., solvent partitioning may need to be repeated one or more times).

It is to be further noted that, in a particular embodiment (and as further illustrated in Scheme 1), the piperidine derivative is a substituted 4-hydroxymethyl-4-aminopiperidine, and more specifically is (4-phenylamino)-1-(2-(thiophen-2-yl)-ethyl-piperidin-4-yl)methanol (compound 2), which is reacted with about a 60% dispersion of sodium hydride (about 1.4:1 molar ratio of sodium hydride to the piperidine compound) in diglyme with a catalytic amount of t-butanol for about 2 hours at a temperature of about 65° C.-70° C. The resulting sodium salt is then methylated using methyl iodide (about a 1.1:1 molar ratio, methyl iodide to the sodium salt) for about 16 hours at a temperature of about 65° C.-70° C. The resulting crude ether (i.e., compound 3), which is (4-methoxymethyl)-N-phenyl-1-(2-(thiophen-2-yl)-ethyl-piperidin-4-amine), may be isolated from the reaction mixture by means generally known in the art, but more particularly may be isolated by the addition of water thereto and then filtering the resulting mixture.

Once isolated, the crude ether may be further purified by a liquid-liquid extraction process using a mixture of an organic and aqueous solvents, such as for example a mixture of toluene and water, the pH thereof (which may or may not be buffered) being adjusted and/or maintained within the range of, for example, between about 4.8 and 5.4 (and preferably between about 5.0 and about 5.2), followed by partitioning of the organic phase soluble piperidine ether intermediate into the aqueous or water phase by adjustment of the pH to within a range of, for example, between about 1.8 and about 2.9 (and preferably between about 2 and about 2.7), by addition of an acid as necessary (such as hydrochloric acid or equivalent) thereto. The water soluble hydrochloride of compound (3) may be converted back to the base and precipitated by adding an appropriate base thereto (e.g., by adding the water soluble hydrochloride to an aqueous, basic solution, such as for example a solution of sodium hydroxide or equivalent), in a quantity sufficient to raise the pH thereof to about 12 or more. The resulting base may then be isolated by means generally known in the art (e.g., by filtration). After compound 3 has been isolated or collected, it may be dried by means generally known in the art (e.g., convection oven at about 50° C. to about 60° C. for about 24 to about 48 hours).

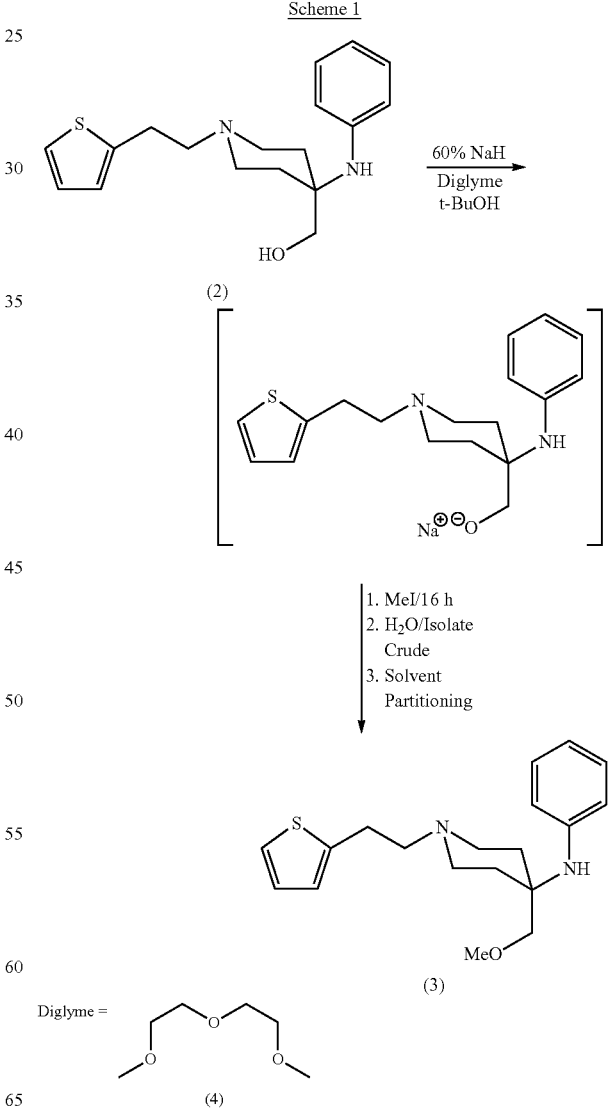

2. Preparation of Piperidine Amide Product

In accordance with the process of the present disclosure, the above-described piperidine ether intermediate may be further modified in order to arrive at the desired piperidine amide compound of formula (C):

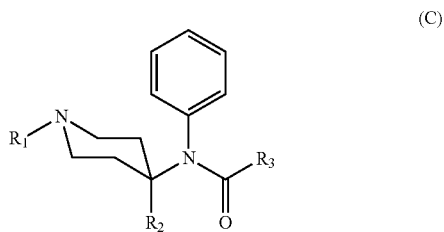

(C)

wherein: $R_1$ and $R_2$ are as previously defined above, and $R_3$ is alkyl (typically $C_1$-$C_5$ alkyl, and in one preferred embodiment is ethyl). In one or more preferred embodiments, the process of the present disclosure is utilized to prepare sufentanil, either in the base form or alternatively in the acid salt form (as detailed elsewhere herein).

As previously noted above, the process of the present disclosure is further directed to one or more of the above-described processes, which additionally comprises contacting the above-described piperidine ether intermediate with an alkyl acid halide in an appropriate organic solvent, followed by quenching the reaction with an appropriate base, in order to form the amide derivative thereof. Selection of an appropriate alkyl acid halide, and/or solvent, and/or base, for the reaction in order to obtain the desired reaction product may be achieved by means generally known in the art (including, for example, in accordance with the disclosure of U.S. Pat. No. 5,489,689, the entire contents of which are incorporated herein by reference for all relevant and consistent purposes). In one preferred embodiment, however, the piperidine ether intermediate is reacted with a $C_1$-$C_5$ alkyl acid halide (e.g., ($C_1$-$C_5$)—COZ, where Z is a halogen, such as F, Cl, Br or I, and in one particularly preferred embodiment the acid halide being propionyl chloride, or $C_2H_5$—COCl) at a molar ratio of, for example, between about 1:1 to about 1:1.3, in an appropriate solvent or solvent mixture (e.g., a mixture of dichloromethane and triethylamine (e.g., about 0.26 equivalents of triethylamine therein), or other suitable organic base). After the reaction has reached a desired point of completion (as determined by means generally known in the art, such as by HPLC), the reaction may be quenched by the addition of a sufficient quantity of a base (e.g., about 2, about 2.5, about 2.75 or more equivalents of base) thereto, such as the addition of a solution of ammonium hydroxide in water thereto.

After the reaction has been quenched, the reaction solvent, and more specifically a portion thereof, may be removed by means generally known in the art, including for example distillation at an appropriate temperature, for a time sufficient to remove some amount, but not all, of the solvent. In this regarding it is to be noted that, as used herein, a "portion" of solvent generally refers to removing between about 50% and less than 100% thereof, and more specifically refers to removing between about 60% and about 90%, or about 70% and about 80%, with removal of about 80% being preferred in various embodiments. Once this portion of the solvent has been removed, an appropriate acid (such as hydrochloric acid or equivalent thereof), may be added to the remaining reaction mixture, and then further solvent removal may occur (e.g., further removal of the organic solvent, such as dichloromethane, by azeotropic distillation until all or nearly all has been removed).

After solvent removal, and more specifically distillation, is complete, the reaction product may be collected. Typically, however, collection of the reaction product includes first recrystallization in situ using means generally known in the art; that is, recrystallization of the reaction product is carried out within the reaction vessel itself, and/or from the remains of the reaction mixture itself, using means generally known in the art. Advantageously, in one particular embodiment, recrystallization need not be repeated a number of times in order to obtain a reaction product of sufficient purity for use directly, or for further processing into the base (as further detailed herein below). Rather, recrystallization of the reaction product may be performed only once.

After recrystallization, the acid salt of the desired reaction product (e.g., the hydrochloric acid salt of sufentanil) may be further purified, and/or converted to the desired base, by for example dissolution in an appropriate solvent (e.g., water, or a mixture of water and an alcohol, such as ethanol), followed by the addition of charcoal (or another decolorizing carbon source) and filtration (after optional addition of a filtering aid, such as celite). The collected product may then be converted to the desired base by means of adding a sufficient quantity of an appropriate base (e.g., sodium hydroxide, potassium hydroxide, ammonium hydroxide, lithium hydroxide, potassium bicarbonate, potassium carbonate, sodium bicarbonate, sodium carbonate or a mixture thereof) to the filtrate solution (such as for example a slight molar excess of sodium hydroxide, based on the molar concentration of the acid salt of the desired reaction product therein). After conversion to the base, the base may be isolated and collected by means generally known in the art.

It is to be noted that, in a particular embodiment (and as further illustrated in Scheme 2, below), the alkyl acid halide is an alkyl acid chloride, and more particularly is propionyl chloride, while the ether derivative that is contacted by the alkyl acid halide (e.g., propionyl chloride) is (4-methoxymethyl)-N-phenyl-1-(2-(thiophen-2-yl)-ethyl-piperidin-4-amine (compound 3), and the resulting amide derivative is sufentanil, either in an acid salt form (e.g., a hydrochloride salt, compound 6) or the base form (compound 1, upon optional neutralization of the acid salt form).

Scheme 2

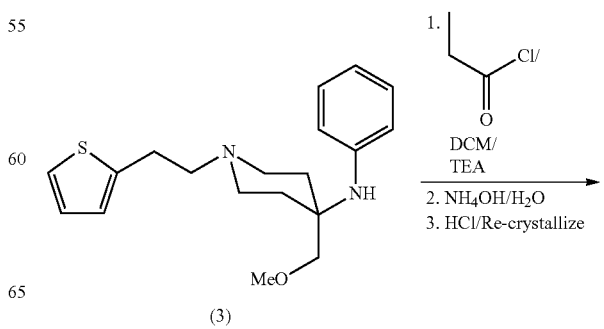

(3)

-continued

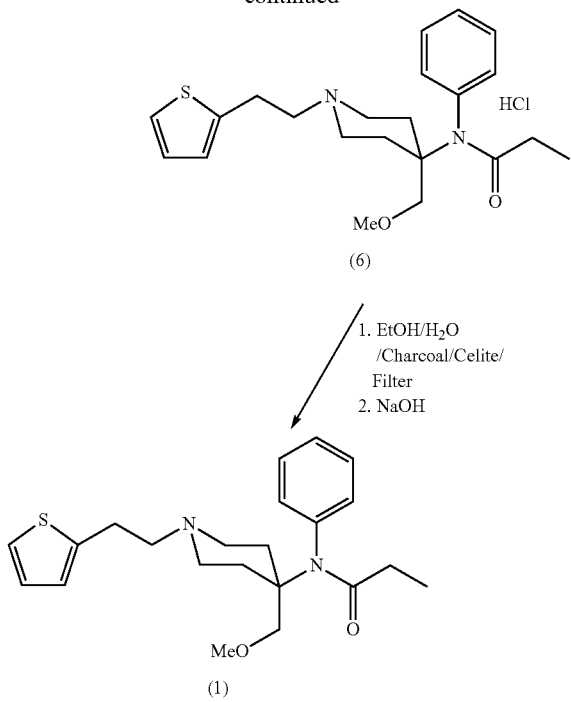

It is also to be noted that, in one or more embodiments, the process of the present disclosure enables an overall yield (of, for example, compound 1 from Scheme 2, based on the starting alcohol, and in this instance specifically compound 2 from Scheme 1), of greater than 55%, and more typically about 65%, about 75%, or more (e.g., about 80%, about 85% or more, with yields typically being between about 55% and about 80%, or about 65% and about 75%). It is to be still further noted that the above-described in situ recrystallization and subsequent purification (e.g., charcoal treatment) provides the desired product having a color and purity that meet or exceed industry standards (such as the International Conference on Harmonisation of Technical Requirements for Registration of Pharmaceuticals for Human Use (ICH)).

EXAMPLES

The processes of the present disclosure are further illustrated by the following Examples. Accordingly, theses should not be viewed in a limiting sense.

1. Preparation of 4-(Methoxymethyl)-N-phenyl-1-(2-(thiophen-2-yl)ethyl)piperidin-4-amine (3)

To a clean dry 2 L flask flushed with a slow flow of nitrogen, sodium hydride (60% dispersion in mineral oil, 11.38 g, 284.4 mmol), followed by (4-(phenylamino)-1-(2-(thiophen-2-yl)ethyl)piperidin-4-yl)methanol (2), (60.00 g, 189.5 mmol), diethylene glycol dimethyl ether (300 mL) and t-butanol (2.53 g, 34.1 mmol) were mixed together using overhead stirring. The mixture was heated to 70° C. for 2 hours and then cooled to 5° C. or below. Methyl iodide (29.60 g, 208.5 mmol) was added at such a rate that the temperature did not exceed 6° C. (For larger runs, it is typically advantageous to pre-mix the methyl iodide with an equal volume of diethylene glycol dimethyl ether to minimize over alkylated material.)

Once the addition was complete (approximately 1.5 hours), the reaction was stirred for a further 16 hours at approximately 5° C. At the end of this time period, 120 mL of DI water was added such that the temperature remained below 10° C. (the first approximately 2 mL being added slowly to allow frothing to dissipate). The reaction was allowed to crystallize, and then a further portion of DI water was added (480 mL). The product was filtered on a Buchner funnel to give an off-white wet powder (84.99 g, 27.09% loss on drying (LOD), 85.93% yield after adjusting for drying and assay). Dried material typically assayed (dry) at 86.91 wt % (3) and had 1.11 wt % of the starting alcohol, (2).

Residual alcohol (2), diglyme and mineral oil are reduced/eliminated by either of the following methods:

A. Buffered System

A pH buffered solution was prepared by dissolving sodium phosphate dibasic (252 g, 1.45 mol) in 1250 mL of DI water, followed by citric acid mono-hydrate (167 g, 794 mmol). The pH of this solution (4.70) was adjusted to 5.0 by the addition of 50% sodium hydroxide solution in water, and then 81.89 g of the previous ether (3) dissolved in toluene (1250 mL) was added. The phases were mixed vigorously and then separated. The aqueous phase was extracted further with toluene (1250 mL), and then combined with the other toluene extract. The combined toluene phase was washed with pH 5.20 buffer, prepared by dissolving sodium phosphate dibasic (26.4 g, 151 mmol) in 1250 mL of DI water followed by citric acid mono-hydrate (14.6 g, 69 mmol). The phases were separated and the toluene phase added to DI water (1250 mL) while stirring. Concentrated hydrochloric in water (265 mL, at 1:10 ratio) was added to adjust the pH to a target of 2.50-2.75 (2.60 actual in this case). Agitation was stopped, and then the layers were allowed to completely phase separate. The aqueous phase was cooled to <17° C. and the pH adjusted with 10% sodium hydroxide (65 mL) to a pH ≥9.00 (10.30 in this case). The product was filtered on a Buchner funnel and washed with DI water (2×250 mL). The wet cake (70.68 g) was dried in a convection oven at 60° C. until constant weight. This yielded 52.64 g of (3); 84.0% yield from (2) as an off-white powder, assaying at 99.20 wt % title product (3) and 0.22 wt % (an 80.18% reduction) of the alcohol (2).

B. Un-buffered System

A crude sample of compound 3 (89.90 g, 89 wt % (dry), 80.01 g effective, containing 0.11 wt % residual alcohol (2)) was dissolved in toluene (860 mL) and transferred to a jacketed glass vessel with an overhead stirrer. DI water (860 mL) was then added. The pH of the aqueous layer was adjusted to 4.95 with 25 mL of dilute hydrochloric acid solution (aliquot from 50 mL of concentrated hydrochloric acid mixed with 450 mL of DI water). The pH of an aliquot of the aqueous layer was checked periodically. The batch was stirred for an additional 15 min. after the pH was adjusted, and the pH was rechecked. The phases were separated, and the small rag kept with the aqueous layer. The aqueous layer was further extracted with toluene (860 mL) and the phases were mixed. The pH of the aqueous layer was adjusted to 4.93 with dilute sodium hydroxide solution (13 mL of 5%). The pH was periodically checked of an aliquot of the aqueous layer. The phases were mixed for an additional 15 min after the pH was adjusted, and the pH rechecked. The phases were separated and the small rag kept with the aqueous layer, and the aqueous layer was discarded.

The toluene layers were combined in the jacketed glass vessel, and DI water (860 mL) was added. The phases were mixed and the pH of the aqueous layer was adjusted to 5.30 with dilute hydrochloric acid solution (aliquot from 50 mL of concentrated hydrochloric acid mixed with 450 mL of DI water). The pH was periodically checked of an aliquot of the aqueous layer. The batch was stirred for an additional 15 min after the pH was adjusted, and the pH was rechecked. The phases were separated and the aqueous layer discarded. To the combined toluene layers, DI water (860 mL) was added. The pH of the aqueous layer was adjusted to 2.68 using dilute hydrochloric acid solution (350 mL, aliquot from 50 mL of concentrated hydrochloric acid mixed with 450 mL of DI water). The batch was stirred an additional 15 min, and the pH rechecked. The pH was 2.69. The phases were allowed to settle for 90 min and the phases were separated. The toluene layer was discarded. The stirred vessel was rinsed with methanol, then with water, to remove all traces of toluene.

To the stirred vessel, DI water (400 mL) was added 400 mL and diluted sodium hydroxide solution (250 mL of 5%). The vessel was cooled to 10° C., and the batch was seeded with a small amount of purified product from a previous run. (Seeding counteracts a tendency of the precipitating product to oil out at first before solidifying; oiled product tends to stick to the reactor and agitator upon solidifying, requiring increased manual intervention in order to be recovered.) The step (3) hydrochloride (aqueous layer) totaling approximately 1300 mL was slowly added over five min (drop-wise addition) until the batch turned cloudy. The addition was stopped for five minutes until a thin slurry formed. Addition was resumed and completed in a total time of approximate 2 hours. The pH of the batch was periodically checked with pH paper during the addition to ensure the pH was above 12. After the hydrochloride was added, the batch was stirred for 0.5 hours then filtered using a 12.5 cm Buchner funnel. The filter cake was washed with room temperature DI water (500 mL). The filter cake was collected in and then dried in a convection oven at 65° C. until constant weight was achieved. The product yield was 78.46 g (96.28 wt %, with the residual alcohol (2) at 0.03 wt %, a 72.73% reduction).

2. N-(4-(Methoxymethyl)-1-(2-(thiophen-2-yl)ethyl) piperidin-4-yl)-N-phenylpropionamide Hydrochloride/Sufentanil Hydrochloride (6)

Purified 4-(methoxymethyl)-N-phenyl-1-(2-(thiophen-2-yl)ethyl)piperidin-4-amine (3), (142.05 g, 429.8 mmol) was dissolved in dichloromethane (1100 mL) and stirred. Propionyl chloride (51.66 g, 558.3 mmol, approximate 1.30 eq) was added and the temperature spiked to 41° C. before cooling and returning to ambient temperature. After 40 min, triethylamine (11.37 g, 112.3 mmol, 0.26 eq) was added and the reaction continued for another 30 min. Concentrated ammonium hydroxide (155 mL) was diluted with DI water (231 mL) and added to the reaction, along with dichloromethane (260 mL). The mixture was stirred vigorously for 30 min, and the layers were separated. The organic (bottom) layer was taken forward. Vacuum (350 Torr) was applied and approximately 80% of the dichloromethane was distilled off at 100-350 Torr/18-40° C. The vacuum was broken with N2 and dilute aqueous hydrochloric acid (1N, 600 mL, 600 mmol, 1.40 eq) and DI water (308 mL) were added. The mixture was stirred vigorously for 1.3 hours. Vacuum was again applied and the remaining dichloromethane was distilled off at 100 Torr and a pot temperature beginning at ambient up to a maximum of 51° C. Once distillation was complete, the vacuum was broken with $N_2$ and the suspension was heated to 85° C., at which point all of the sufentanil hydrochloride dissolved. The solution was stirred and allowed to cool to 80° C., where all of the product still remained in solution. The solution was seeded with approximately 50 mg of sufentanil hydrochloride, and allowed to cool at about 30° C. per hour (by 75° C. considerable crystallization had occurred). The system was held at 75° C. for 10 minutes before cooling further, after which it was allowed to cool to ambient, a process occurring over an hour or more. The product suspension was left at ambient temperature overnight, then cooled to 1° C. on an ice bath and kept there for 1.1 h. The white product was filtered and the cake was washed with cold (3° C.) DI water (273 mL). The cake was air-dried for 30 minutes and dried in a vacuum oven overnight (100 Torr, 65° C.); this gave the title product as a white powder (169.4 g, 93.16% yield as is). The crude sufentanil hydrochloride was used without further purification.

3. N-(4-(Methoxymethyl)-1-(2-(thiophen-2-yl)ethyl) piperidin-4-yl)-N-phenylpropionamide Sufentanil Base (1)

Sufentanil hydrochloride (150.68 g, 356.2 mmol) was dissolved in 3A ethanol (400 mL) and deionized water (500 mL) by heating to approximately 40° C. Activated charcoal (15.00 g) and Celite (7.40 g) were added and the suspension was stirred for approximately 3 minutes. Separately a bed of Celite (7.60 g) was prepared by washing with deionized water (200 mL) followed by methanol (200 mL) to facilitate drying. The sufentanil hydrochloride-charcoal suspension was filtered through the Celite pad, and washed with a mixture of ethanol (200 mL) in water (400 mL). The color of the filtrate was noticeably less yellow than the color of the sufentanil solution prior to the introduction of the activated charcoal. The pH of the filtrate was 2.51. Sodium hydroxide (3M, approximately 8 mL) was added slowly with stirring until the system became persistently cloudy, about pH 5.73. The base addition was paused for 30 minutes, by which time enough precipitate had formed that the pH probe was no longer visible through the suspended solids, although the suspension was still rather thin. During this time, the pH dropped to 5.55. Sodium hydroxide addition was resumed at a slow rate until the pH was 6.94, then paused again for 30 minutes. Total use of 3M sodium hydroxide to this point was approximately 113 mL. Sodium hydroxide addition was then resumed until the pH exceeded 12 (12.09 actual), which brought the total sodium hydroxide added to approximately 118 mL. The sufentanil base suspension was cooled in an ice bath to 1.5-5° C. and stirred for 30 minutes. The product was filtered, washed with cold (5° C.) DI water (525 g), air dried for 5 min. The wet cake was dried in the vacuum oven overnight (100 Torr, 60° C., 16 h), to yield 132.86 g (96.49%) of ICH compliant sufentanil base as a white powder.

In view of the above, it will be seen that the several advantages of the disclosure are achieved and other advantageous results attained. As various changes could be made in the above processes without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

What is claimed is:

1. A process for preparing a compound of Formula (3),

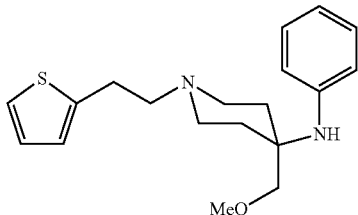

(3)

the process comprising:
(i) contacting a substituted 4-hydroxymethyl-4-aminopiperidine of Formula (2)

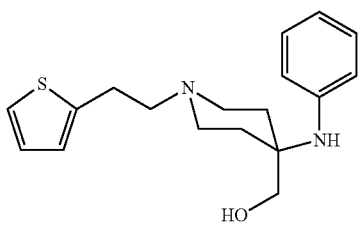

(2)

with a dispersion comprising between about 50 and about 70% by weight (based on the total weight of the dispersion) alkali metal hydride in the presence of an alcohol catalyst and an organic solvent selected from the group consisting of N,N-dimethyl tormamide (DMF), 1methyl-2-pyrrolidinone (NMP), dimethoxy ethane (glyme), diethylene glycol diethyl ether (diglyme), dimethyl sulfoxide (DMSO), and combinations thereof, to deprotonate the hydroxyl group of the substituted 4-hydroxymethyl-4-aminopiperidine; and,
(ii) reacting an alkylating agent with the deprotonated, substituted 4-hydroxymethyl-4 aminopiperidine to form the compound of Formula (3).

2. The process of claim 1, wherein the alkylating agent is a methylating agent.

3. The process of claim 1, wherein the alcohol catalyst is selected from the group consisting of methanol, ethanol, isopropanol, t-butanol or a combination thereof.

4. The process of claim 1, wherein the alcohol catalyst is t-butanol, and further wherein the deprotonated, substituted 4-hydroxymethyl- 4-aminopiperidine is reacted with a methyl iodide alkylating agent.

5. The process of claim 1, wherein the organic solvent is diglyme.

6. The process of claim 1, wherein the dispersion comprises between about 55% and about 65% by weight alkali metal hydride.

7. The process of claim 6, wherein the dispersion comprises about 60% by weight sodium hydride in mineral oil.

8. The process of claim 1, further comprising:
(i) dilution of a reaction mixture containing the compound of Formula (3) with water;
(ii) isolating the compound of Formula (3) from the diluted reaction mixture;
(iii) purifying the isolated compound of Formula (3) by liquid-liquid extraction, the isolated compound of Formula (3) being contacted with a solvent system comprising an organic phase and an aqueous phase at a pH between about 4.8 and about 5.4, and then the organic phase soluble compound of Formula (3) being partitioned into the aqueous phase by adjusting the pH to between about 1.8 and about 2.9; and,
(iv) isolating the partitioned compound of Formula (3) from the aqueous phase by adjusting the pH thereto to greater than about 12 by the addition of a base thereto.

9. The process of claim 8, wherein the pH of the solvent system is between about 5.0 and about 5.2, and further wherein the pH is adjusted to between about 2.0 and about 2.7 to partition the compound of Formula (3) into the aqueous phase; and the partitioned compound of Formula (3) is isolated by adjusting the pH of the aqueous phase by the addition of a base selected from the group consisting of ammonium hydroxide, sodium hydroxide, potassium hydroxide, lithium hydroxide, potassium bicarbonate, potassium carbonate, sodium bicarbonate, sodium carbonate or a mixture thereof.

10. A process for preparing an amide of Formula (C) comprising:
(i) contacting a compound of Formula (2) with a dispersion comprising between about 50% and about 70% by weight (based on the total weight of the dispersion) alkali metal hydride in the presence of an alcohol catalyst and an organic solvent to deprotonate the hydroxyl group of the compound of Formula (2);
(ii) reacting an alkylating agent with the deprotonated compound of Formula (2) to form the compound of Formula (3);
(iii) contacting the compound of Formula (3) with an alkyl acid halide in an organic solvent to form the amide of Formula (C);
(iv) removing a portion of the organic solvent from the amide of Formula (C); and,
(v) collecting the amide of Formula (C);

wherein Formula (C), Formula (2), and Formula (3) are as follows:

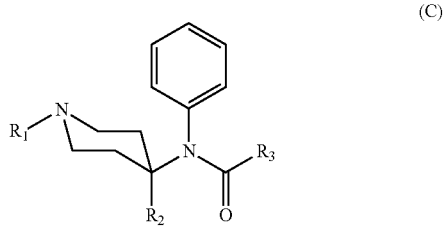

(C)

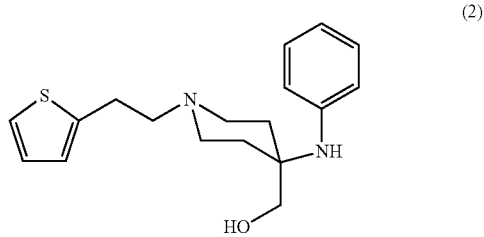 [SMILES: OCC1(Nc2ccccc2)CCN(CCc2cccs2)CC1]

(2)

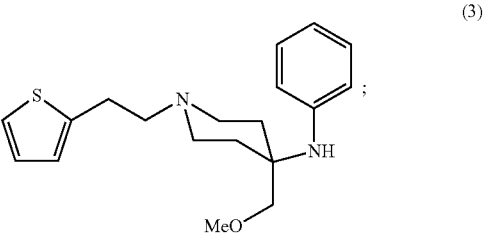

(3)

and wherein $R_1$ is 2-thiophen-2-ylethyl; $R_2$ is methoxymethyl; and $R_3$ is a $C_1$-$C_5$ alkyl.

11. The process of claim 10 wherein about 70% to about 80% (by weight) of the organic solvent is removed from the amide of Formula (C) by distillation; and the alkyl acid halide is propionyl chloride.

12. The process of claim 11, wherein after a portion of the organic solvent has been removed, an acid is added to the amide of Formula (C) to form an acid salt thereof.

13. The process of claim 12 wherein a base is added to the acid salt of the amide of Formula (C), to form a base of the amide of Formula (C).

14. The process of claim 13, wherein the resulting base of the amide of Formula (C) is a sufentanil base.

* * * * *